(12) United States Patent
Loose et al.

(10) Patent No.: US 10,088,454 B2
(45) Date of Patent: Oct. 2, 2018

(54) SPEED OF SOUND AND/OR DENSITY MEASUREMENT USING ACOUSTIC IMPEDANCE

(71) Applicant: CiDRA Corporate Services Inc., Wallingford, CT (US)

(72) Inventors: Douglas H. Loose, Southington, CT (US); Lambertus J Didden, Glastonbury, CT (US); Alan D. Kersey, South Glastonbury, CT (US)

(73) Assignee: CiDRA CORPORATE SERVICES, INC., Wallingford, CT (US)

( * ) Notice: Subject to any disclaimer, the term of this patent is extended or adjusted under 35 U.S.C. 154(b) by 0 days.

(21) Appl. No.: 14/387,732

(22) PCT Filed: Apr. 5, 2013

(86) PCT No.: PCT/US2013/035471
§ 371 (c)(1),
(2) Date: Sep. 24, 2014

(87) PCT Pub. No.: WO2013/152302
PCT Pub. Date: Oct. 10, 2013

(65) Prior Publication Data
US 2015/0082862 A1 Mar. 26, 2015

Related U.S. Application Data

(60) Provisional application No. 61/620,788, filed on Apr. 5, 2012, provisional application No. 61/658,628, filed on Jun. 12, 2012.

(51) Int. Cl.
G01N 29/028 (2006.01)
G01N 33/38 (2006.01)

(52) U.S. Cl.
CPC ......... G01N 29/028 (2013.01); G01N 33/383 (2013.01); *G01N 2291/0251* (2013.01)

(58) Field of Classification Search
CPC .......................... G01N 29/028; G01N 33/383
See application file for complete search history.

(56) References Cited

U.S. PATENT DOCUMENTS

| | | | |
|---|---|---|---|
| 1,795,647 A * | 3/1931 | Flanders | H04R 29/00 73/589 |
| 5,343,752 A | 9/1994 | Woyski et al. | |

(Continued)

*Primary Examiner* — Justin Olamit
(74) *Attorney, Agent, or Firm* — Ware, Fressola, Maguire & Barber LLP (57) ABSTRACT

Apparatus is provided featuring a signal processor or signal processing module configured at least to: receive signaling containing information about a radiation impedance of a piston vibrating a process medium, including a fluid or slurry; and determine a speed of sound or density measurement related to the process medium, based at least partly on the signaling received. The signal processor or signal processing module may determine a speed of sound measurement related to the process medium, based on at least partly on the density of the process medium, including where the density of the process medium is known, assumed or determined by the signal processor or signal processing module, or determine a density measurement related to the process medium, based on at least partly on the speed at which sound travels in the process medium, including where the speed of sound of the process medium is known, assumed or determined by the signal processor or signal processing module.

33 Claims, 6 Drawing Sheets

(56) References Cited

U.S. PATENT DOCUMENTS

| | | | |
|---|---|---|---|
| 5,527,175 | A | 6/1996 | Face, Jr. et al. |
| 5,943,234 | A | 8/1999 | Martinez et al. |
| 7,134,320 | B2 | 11/2006 | Gysling et al. |
| 7,165,464 | B2 | 1/2007 | Gysling et al. |
| 7,343,820 | B2 | 3/2008 | Gysling et al. |
| 7,363,800 | B2 | 4/2008 | Gysling et al. |
| 7,366,621 | B2 | 4/2008 | Sprague |
| 7,367,240 | B2 | 5/2008 | Gysling et al. |
| 7,426,852 | B1 | 9/2008 | Rothman |
| 7,617,716 | B2 * | 11/2009 | Gysling ............... G01F 1/666 73/19.03 |
| 9,423,379 | B2 * | 8/2016 | Cordeiro ............ E21B 47/0005 |
| 2007/0175273 | A1 | 8/2007 | Follini et al. |
| 2009/0205427 | A1 | 8/2009 | Lootens et al. |
| 2010/0071477 | A1 | 3/2010 | Haehner et al. |
| 2013/0192351 | A1 * | 8/2013 | Fernald ................ G01F 1/7082 73/61.49 |

\* cited by examiner

Apparatus 10:

> Signal processor 10a configured to
>
> receive signaling containing information about a radiation impedance of a piston vibrating a process medium, including a fluid or slurry;
>
> determine a speed of sound or density measurement related to the process medium, based at least partly on the signaling received; and/or
>
> provide corresponding signaling containing information about the speed of sound or density measurement related to the process medium > Other signal processing modules 10b for implementing the signal processing functionality according to the present invention, including memory for storing a computer program code, input/output modules, and data and control busing architecture for coupling all the signal processing component together

Apparatus 50:

Signal processor 50a configured to receive signaling containing information about a compressibility (1/β) of a process flow medium, including a fluid or slurry, flowing in a process pipe, and about a speed at which sound travels within the process flow medium;

determine a density of the process flow medium, based at least partly on the signaling received; and/or provide corresponding signaling containing information about the density of the process flow medium.

Other signal processing modules 50b for implementing the signal processing functionality according to the present invention, including memory for storing a computer program code, input/output modules, and data and control busing architecture for coupling all the signal processing component together

Figure 2a

Figure 2b: Concept for using a combined SONARtrac SOS measurement system along with a fluid compressibility measurement probe.

SPEED OF SOUND AND/OR DENSITY MEASUREMENT USING ACOUSTIC IMPEDANCE

CROSS-REFERENCE TO RELATED APPLICATIONS

This application corresponds to international patent application serial no. PCT/US2013/035471, filed 5 Apr. 2013, which claims benefit to provisional patent application Ser. No. 61/620,788, filed 5 Apr. 2012, entitled "Speed of sound and/or density measurement using acoustic impedance;" and Ser. No. 61/658,628, filed 12 Jun. 2012, entitled "Determination of the density of a process flow fluid/slurry using both speed of sound and fluid compressibility measurements," which are both incorporated by reference in their entirety.

This application also relates to U.S. patent application Ser. No. 13/583,062, filed 12 Sep. 2012, which is a national stage application corresponding to PCT/US11/27731, which are both incorporated in their entirety by reference, and assigned to the assignee of the present application.

This application also relates to Patent Cooperation Treaty application serial no. PCT/US12/60822, filed 18 Oct. 2012, claiming benefit to U.S. provisional patent application Ser. No. 61/548,549, filed 18 Oct. 2011, which are both incorporated in their entirety by reference, and assigned to the assignee of the present application.

BACKGROUND OF THE INVENTION

1. Field of Invention

The present invention relates to a technique for real time air measurement in wet concrete; more particularly related to a technique for real time air measurement in wet concrete in order to control the amount of air in a mixture of concrete.

2. Description of Related Art

The measurement of density in process industries is important in a wide range of applications, including: chemical processing, refining, food processing, mining, dredging, and waste water processing. In many applications, the current technology of choice is a Nuclear Density meter. Due to the use of an active nuclear source (gamma ray) in these meters, these devices require a certain degree of regulatory oversight, including training, specialized personnel, and handling/disposal procedures etc. Consequently, there is a push in many industries to replace Nuclear Density Measurement with Non-Nuclear devices.

The assignee of the present application has developed a platform technology, sold under the product name, SONARtrac™, that measures the speed at which sound travels within a fluid or slurry (e.g., the speed at which compressional waves propagate through a fluid). The technique has proven to provide a very robust measurement and has been applied to a range of applications in industrial processing, particularly where the entrained air and/or gas measurements are of interest.

While the measurement of the speed of sound (SOS) in a fluid can be used to give a measure of the constituents of a flow (for example oil-water in an oil production application), it's direct use for density measurement is limited unless there is a priori knowledge of the density of the component constituents (or "phases") of the process flow stream.

Speed of Sound Measurement

Moreover, in the prior art, a number of techniques have been developed that rely on measuring the speed of sound through a material flowing through a pipe. These techniques include using a known SONAR-based GVF meter, density meter and potential mass fraction meter. In these techniques, a passive array-based sensor system is used to detect the presence and speed of acoustics traveling through the materials contained within a pipe. These materials can range from single phase homogeneous fluids to two or three phase mixtures of gases, liquids and solids. Since the measurements system is passive it relies on acoustics produced externally for the measurement. These acoustics can often times come from other equipment in or attached to the pipe such as pumps or valves.

Moreover, in these known techniques many times chemical additives may be added, including to a known flotation process in mineral processing to aid in the separation of the ore. The chemicals, known as frothers, control the efficiency of the flotation process by enhancing the properties of the air bubbles. An important parameter in flotation optimization is the gas volume fraction within a flotation cell. U.S. Pat. No. 7,426,852 B1, which is hereby incorporated by reference in its entirety, discloses approaches to make this measurement, and discloses a technique whereby the speed of sound in the aerated fluid is locally measured using a waveguide (pipe) in conjunction with a SONAR-based array. From the speed of sound measurement, the gas volume fraction can be calculated.

By way of example, see other techniques related to the use of such SONAR-based technology disclosed, e.g., in whole or in part in U.S. Pat. Nos. 7,165,464; 7,134,320; 7,363,800; 7,367,240; and 7,343,820, all of which are incorporated by reference in their entirety.

Moreover, air is a very important component of many materials, such as viscous liquids, slurries or solids, and mixtures of concrete. In particular, air is a critical ingredient when making concrete because it greatly improves the cured product damage resistance to freeze/thaw cycles. Chemical admixtures are typically added during mixing to create, entrain and stabilize billions of small air bubbles within the concrete. However, the entrained air in concrete has the disadvantage of reducing strength so there is always a trade-off to determine the right amount of air for a particular application. In order to optimize certain properties of concrete, it is important to control the entrained air present in the wet (pre-cured) concrete. Current methods for measuring the entrained air can sometimes be slow and cumbersome and additionally can be prone to errors. Moreover, the durability of concrete may be enhanced by entraining air in the fresh mix. This is typically accomplished through the addition of chemical admixes. The amount of admix is usually determined through empirical data by which a "recipe" is determined. Too little entrained air reduces the durability of the concrete and too much entrained air decreases the strength. Typically the nominal range of entrained air is about 5-8% by volume, and can be between 4% and 6% entrained air by volume in many applications. After being mixed in the mixer box, the concrete is then released to the truck. The level of entrained air is then measured upon delivery of the mix to the site. The draw back of the current method is that the mix is committed to the truck without verification of that the air level in the mix is within specification.

The aforementioned U.S. patent application Ser. No. 13/583,062 discloses techniques for real time air measurement in wet concrete in concrete a rotary drum mixer, including implementing sensing technology in a hatch cover, as well as a stationary concrete mixer using an integrated sound source and two receivers, using SONAR-based technology developed and patented by the assignee of the instant patent application as well as that application.

SUMMARY OF THE INVENTION

The present invention sets forth new technique, including methods and apparatuses, to measure the density and/or speed of sound of a fluid or slurry by measuring an acoustic reaction force on a vibrating piston. Both of these parameters can be useful measurements for many industrial processes. For example, in the concrete manufacturing industry, knowing the speed of sound of wet concrete can be used to determine the volume percent of air contained in the concrete. The density can be used to determine that the proper mix was used.

CCS-0084

Speed of Sound and/or Density Measurement Using Acoustic Impedance

By way of example, and according to some embodiments, the present invention may include or take the form of apparatus featuring a signal processor or signal processing module configured at least to:

receive signaling containing information about a radiation impedance of a piston vibrating a process medium, including a fluid or slurry; and determine a speed of sound or density measurement related to the process medium, based at least partly on the signaling received.

According to some embodiments, the present invention may include one or more of the following features:

The signal processor or signal processing module may be configured to determine a speed of sound measurement related to the process medium, based on at least partly on the density of the process medium, including where the density of the process medium is known, assumed or determined by the signal processor or signal processing module.

The signal processor or signal processing module may be configured to determine a density measurement related to the process medium, based on at least partly on the speed at which sound travels in the process medium, including where the speed of sound of the process medium is known, assumed or determined by the signal processor or signal processing module.

The signal processor or signal processing module may be configured to determine a volume percentage of air contained in the process medium, based at least partly on a speed of sound measurement determined.

The signal processor or signal processing module may be configured to determine a speed of sound measurement in the process medium based at least partly on a time of flight measurement technique.

The signal processor or signal processing module may be configured to determine a proper mix or mixture of the process medium based at least partly on a density measurement related to the process medium.

The signal processor or signal processing module may be configured to determine the proper mix or mixture of a wet concrete, based at least partly determining the density of a wet concrete.

The signal processor or signal processing module may be configured to determine the density of the wet concrete, based at least partly on knowing, assuming or determining the speed of sound in the wet concrete.

The signal processor or signal processing module may be configured to determine the speed of sound in the wet concrete based at least partly on a time of flight measurement technique.

The slurry may be a wet concrete, pulp slurry, or food processing slurry.

The signalling received containing information about the radiation impedance may contain information about a motion of the piston being measured and a force required to drive the piston also being measured.

The motion may include the velocity, acceleration or displacement of a harmonically vibrating piston.

The signal processor or signal processing module may be configured to determine the radiation impedance, based at least partly a ratio of the force exerted by a harmonically vibrating piston on the process medium to a velocity of the harmonically vibrating piston.

The apparatus may include a transducer apparatus or device configured with the piston vibrating the process medium and acting as an acoustic source.

The transducer apparatus or device may include a stationary rigid wall surrounding the piston so as to generate a pressure field in a hemisphere forward of the stationary rigid wall.

The transducer apparatus or device may include a motion-sensing transducer having a linear coil and a linear coil actuator or processor configured to measure the motion of the piston, and/or either an inline force-sensing transducer configured to measure the force required to drive the piston, or a measuring device configured to measure the electrical power driving the piston.

The transducer apparatus or device may include a combination of a linear voice coil and a linear voice coil actuator configured to drive the piston, including where the current going to and driving the linear coil is proportional to the force generated.

The signal processor or signal processing module may be configured to provide corresponding signal containing information about the speed of sound or density measurement related to the process medium.

According to some embodiments, the present invention may take the form of a method featuring steps for receiving in a signal processor or signal processing module signaling containing information about a radiation impedance of a piston vibrating a process medium, including a fluid or slurry; and determining in the signal processor or signal processing module a speed of sound or density measurement related to the process medium, based at least partly on the signaling received.

According to some embodiments, the present invention may take the form of apparatus featuring means for receiving signaling containing information about a radiation impedance of a piston vibrating a process medium, including a fluid or slurry; and means for determining a speed of sound or density measurement related to the process medium, based at least partly on the signaling received.

CCS-0084 and 95

According to some embodiments, the signaling may contain information about a compressibility ($1/\beta$) of the process medium and a speed at which sound travels within the process medium; and the signal processor or signal processing module may be configured to determine a density measurement of the process medium, based at least partly on the signaling received, and consistent with that set forth below. Moreover, according to some further embodiments, the present invention set forth above may include one or more of the features set forth below alone or in combination, including processing mediums in process flow pipes or some other processing containers.

CCS-0095

Determination of Density of a Process Flow Fluid/Slurry Using Both Speed of Sound and Fluid Compressibility Measurements According to some embodiments, the present invention may take the form of apparatus featuring a signal processor or signal processing module configured at least to:

receive signaling containing information about a compressibility ($1/\beta$) of a process flow medium, including a fluid or slurry, flowing in a process flow pipe, and about a speed at which sound travels within the process flow medium; and determine a density of the process flow medium, based at least partly on the signaling received.

According to some embodiments, the present invention may include one or more of the following features:

The signal processor or signal processing module may be configured to determine the compressibility ($1/\beta$) of the process flow medium based at least partly first signaling received from a ported unit configured in the process flow pipe to measure the compressibility ($1/\beta$) of the process flow medium.

The apparatus may include the ported unit that measures the compressibility ($1/\beta$) of the process flow medium.

The ported unit may be configured as a compressibility probe that comprises a piston that is used to provide a localized compressibility test of the process flow medium.

The piston may be driven by an actuator and pushed into the process flow medium, including in an oscillatory fashion, or pulsed at a certain repetition rate.

The motion/displacement of the piston may be substantially smaller in relation to the scale of the pipe, including a displacement of about 100-300 microns.

The first signaling may contain information about a local compressibility of the process flow medium, based at least partly on the fact that, as the piston is pushed into the process flow medium in a repetitive mode, the process flow medium surrounding the compressibility probe does not effectively have time to respond; and the compressibility probe may be configured to determine a dynamic response, including a force to move the piston a given distance, of the piston based at least partly on the first signaling received.

The compressibility probe may be configured to measure: the force on the piston, and either the displacement or acceleration of the piston, where the acceleration of the piston is related back to the motion of the piston.

The compressibility probe may be configured to determine the local compressibility of the process flow medium, based at least partly on corresponding measurements providing a measure of a spring constant, or spring rate, of the system, which comprises the stiffness of a mechanical assembly supporting the piston and the stiffness of the process flow medium local to the piston, so that if the stiffness of the mechanical assembly is known, including through calibration without a backing fluid, the local compressibility of the process flow medium can be inferred from the corresponding measurements made.

The signal processor or signal processing module may be configured to determine the compressibility of the process flow medium based at least partly second signaling received from a SONAR-based array that measures the speed at which sound travels within the process flow medium, including based at least partly on the speed at which compressional waves propagate through the process flow medium.

The apparatus may include the SONAR-based array.

The signal processor or signal processing module may be configured to determine the density $\rho$ of the process flow medium, based at least partly on the equation:

$$\rho = \frac{\beta}{c^2},$$

where
c is speed of sound speed at which sound travels within the process flow medium and
$\beta$ is the bulk modulus of the process flow medium.

The SONAR-based array may be configured to determine a volumetric flow rate of the process flow medium flowing in the process pipe.

The signal processor or signal processing module may be configured to determine a mass flow of the process flow medium in the process pipe, based at least partly on the combination of the volumetric flow measurement and a density measurement.

The signal processor or signal processing module may be configured to provide corresponding signal containing information about the density of the process flow medium.

According to some embodiments, the present invention may take the form of a method featuring steps for receiving in a signal processor or signal processing module signaling containing information about a compressibility ($1/\beta$) of a process flow medium, including a fluid or slurry, flowing in a process pipe, and about a speed at which sound travels within the process flow medium; and determining in the signal processor or signal processing module a density of the process flow medium, based at least partly on the signaling received.

According to some embodiments, the present invention may take the form of apparatus featuring means for receiving signaling containing information about a compressibility ($1/\beta$) of a process flow medium, including a fluid or slurry, flowing in a process pipe, and about a speed at which sound travels within the process flow medium; and means for determining a density of the process flow medium, based at least partly on the signaling received.

Moreover, according to some embodiments, the signal processor or signal processing module may be configured with at least one processor and at least one memory including computer program code, the at least one memory and computer program code configured, with the at least one processor, to cause the apparatus at least to receive the signaling and determine the parameter related to the process medium, based at least partly on the signaling received.

The present invention makes important contributions to this current state of the art for real time speed of sound and density measurements of a process medium, including providing important contributions to this current state of the art for air measurement in wet concrete. For example, the present application may provide new means, techniques or ways of real time measurement of entrained air in wet concrete, consistent with and further building on that set forth in the aforementioned U.S. patent application Ser. No. 13/583,062, filed 12 Sep. 2012.

BRIEF DESCRIPTION OF THE DRAWING

The drawing includes FIGS. 1-2b, which are not necessarily drawn to scale, as follows.

DETAILED DESCRIPTION OF BEST MODE OF THE INVENTION

CCS-0084: FIGS. 1a-1d

Figure 1A:
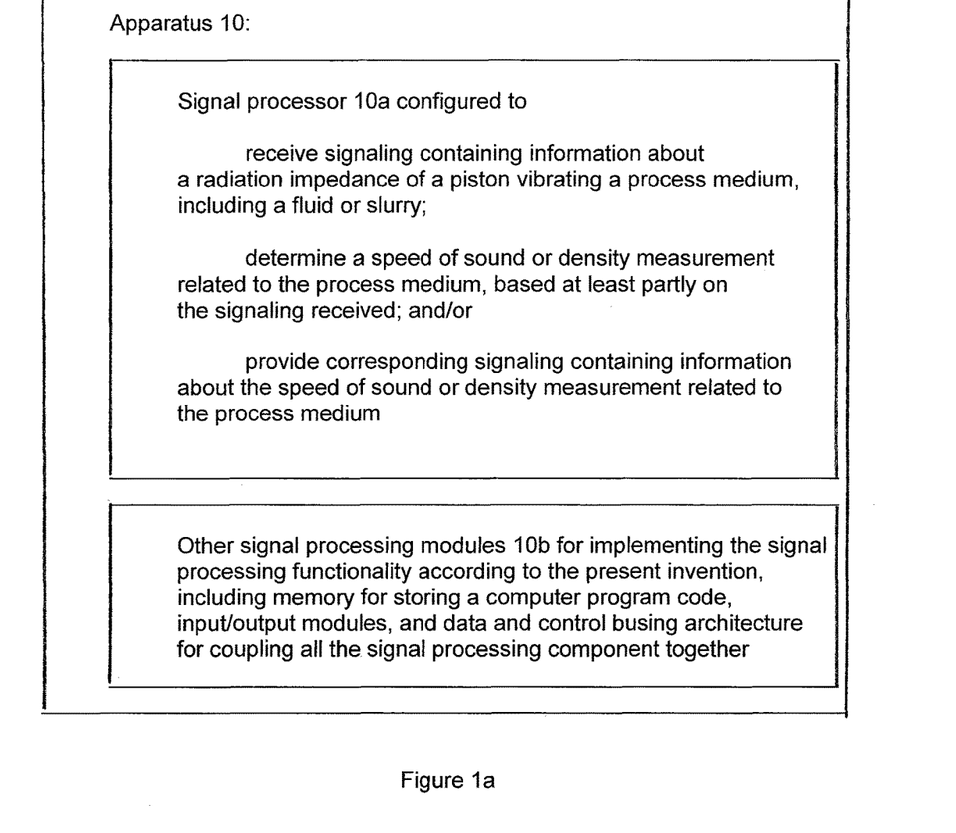
FIG. 1a is a block diagram of a signal processor or signal processing module, according to some embodiments of the present invention.

FIG. 1a shows apparatus generally indicated as 10 according to some embodiments of the present invention. The apparatus 10 may include a signal processor or signal processing module 10a configured to receive signaling containing information about a radiation impedance of a piston vibrating a process medium, including a fluid or slurry; and determine a speed of sound or density measurement related to the process medium, based at least partly on the signaling received.

The signal processor or signal processing module 10a may also be configured to providing corresponding signaling containing information about the speed of sound or density measurement related to the process medium.

By way of example, a person skilled in the art would appreciate that radiation impedance may be understood to mean, or may be defined as, the ratio of the force a radiator exerts on a process flow medium to the velocity of the radiator.

Figure 1B:
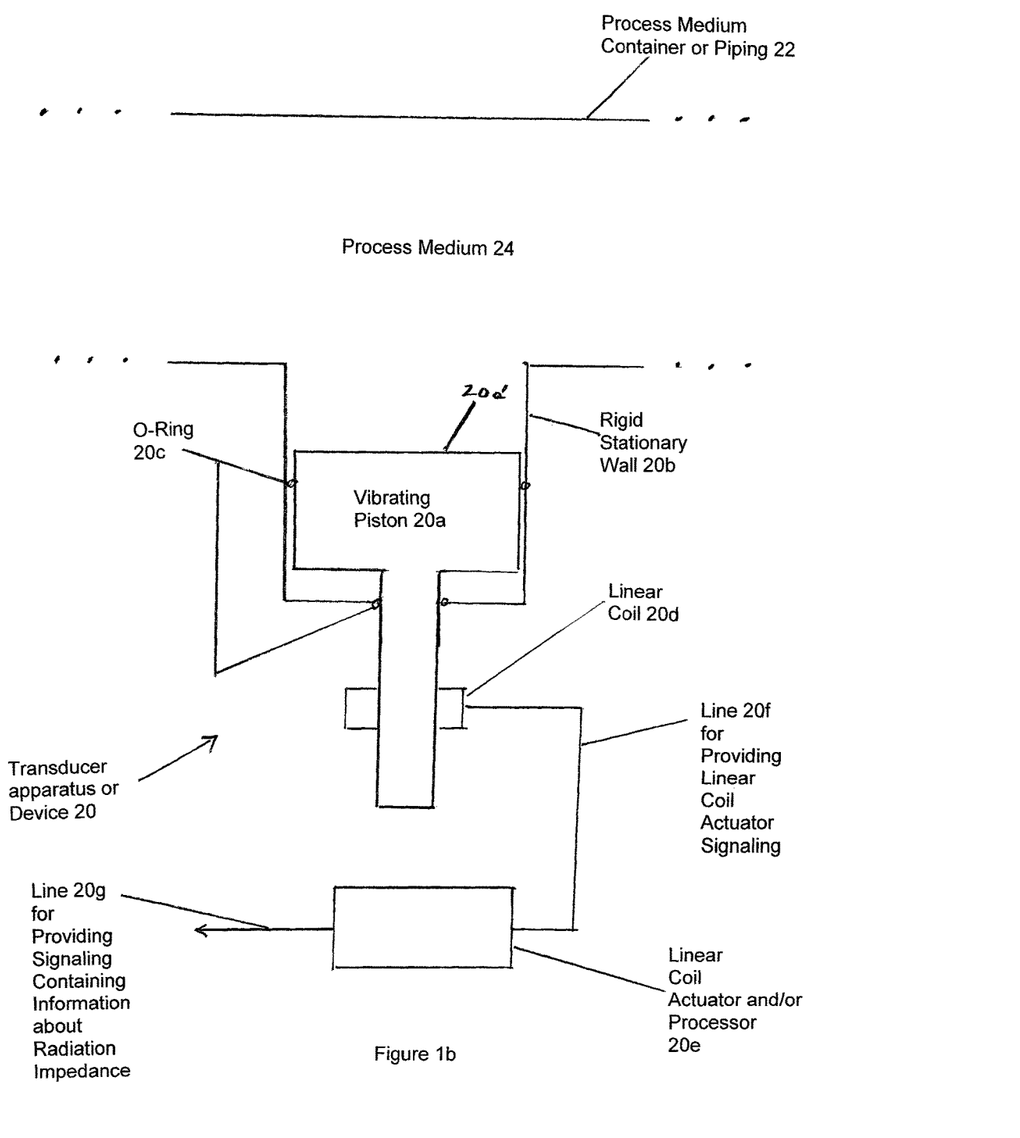
FIG. 1b is an illustration of a transducer apparatus or device arranged in relation to a process medium container or piping, according to some embodiments of the present invention.

FIG. 1b: The Vibrating Piston

By way of example, and according to some embodiments of the present invention, FIG. 1b shows a transducer apparatus or device generally indicated by arrow 20 arranged in relation to a process medium container or piping 22 having a process medium contained or flowing therein. In FIG. 1b, the transducer apparatus or device 20 includes a vibrating piston 20a surrounded by a stationary rigid wall 20b that will act as an acoustic source, generating a pressure field in the hemisphere forward of the wall 20b. By way of example, assuming the piston vibration is time harmonic the velocity of the piston face 20a' is described by the equation:

$$u_p(t) = u_0 e^{j\omega t}, \quad (1)$$

where:
$u_p$=piston face velocity,
$u_0$=velocity amplitude,
$\omega$=angular frequency and
t=time.

Alternatively, the motion of the piston 20a could be described by either its acceleration or displacement with:

$$a_0 = u_0 \omega \quad (2)$$

or:

$$A_0 = \frac{u_0}{\omega} \quad (3)$$

where:
$a_0$=the acceleration amplitude and
$A_0$=the displacement amplitude.

The total force that acts on the face of a time-harmonic vibrating baffled piston in contact with an acoustic fluid or medium 24 is given by:

$$F = \pi a^2 P_{avg} = \pi a^2 u_0 Z_p \quad (4)$$

where:
a=piston radius,
$P_{avg}$=average pressure amplitude on the face of the piston,
$u_0$=piston velocity amplitude, and
$Z_p$=piston radiation impedance.

The radiation impedance of the piston 20a is given by:

$$Z_p = \rho_0 c_0 \left[ 1 - \frac{2J_1(2ka)}{2ka} + i\frac{2K_1(2ka)}{2ka} \right] \quad (5)$$

where:
$\rho_0$=medium density,
$c_0$=medium sound velocity,
k=wavenumber=$\omega/c_0$.
$J_1$=Bessel function of the first kind, and
$K_1$=Struve function.

Note that $Z_p$ is a function of density, sound velocity frequency and piston radius only. At large values of 2ka (piston diameter large compared to the acoustic wavelength) equation (5) reduces to:

$$Z_p = \rho_0 c_0 \quad (6)$$

Sound Velocity and/or Density Measurement

In operation, and by way of example, the vibrating piston 20a may be installed such that it is in contact with the process medium or fluid 24 (or slurry in the case of wet concrete, pulp slurry or food processing slurry, for example) of interest. The piston 20a may be vibrated harmonically as give in equation (1). In FIG. 1b, by way of example, O-rings 20c may be arranged between the vibrating piston 20a and the rigid stationary wall 20b. In addition, a linear coil 20d may be configured to respond to a linear coil actuator signaling along line 20f provided by a linear coil actuator and/or processor 20e for vibrating the piston 20a. The motion of the piston 20a (velocity, acceleration or displacement) may be measured with the appropriate transducer, e.g., by the linear coil actuator and/or processor 20e. In addition, the force required to drive the piston 20a may also be measured. This measuring could be done by an inline force transducer that may include, e.g., the combination of the linear coil 20d and linear coil actuator and/or processor 20e, or by measuring the electrical driving power. In particular, if the piston 20a is driven with the combination of the linear coil 20d and the linear voice coil actuator 20e, the current going or provided to the linear coil 20d is proportional to the force generated.

Rearranging equation (4) to solve for the radiation impedance gives:

$$Z_p = \frac{F}{\pi a^2 u_0} \qquad (7)$$

For a known radius piston vibrating at a known frequency, inserting the measured force less any dynamic forces, F, and the velocity amplitude, $u_0$, or alternatively $a_0$ or $A_0$ substituting equations (2) and (3), the radiation impedance may be determined. Once the radiation impedance is known, the quantity $\rho_0 c_0$ can be found from equation (5). If the density is known or assumed the sound velocity can be determined. Alternatively, if the sound velocity is known or assumed, the density can be determined. By way of example, and as a person skilled in the art would appreciate, the density or speed of sound of the process medium may be known or assumed, e.g., based at least partly on the process medium coming from, or form part of, known batch processing techniques having known or assumed characteristics, and/or from tables or charts containing information about known process medium. The scope of the invention is not intended to how the density or speed of sound of the process medium may be known or assumed. One possibility is to use the time of flight measurement (e.g., see patent application Ser. No. 13/583,062 to determine sound velocity then use the present method to determine density.

In FIG. 1b, linear coil actuator and/or processor may be configured to provide the signaling containing information about the radiation impedance of the piston 20a vibrating the process medium 24 along line 20g, e.g., to the signal processor or processing module 10a in FIG. 1a. In operation, the signal processor or signal processing module 10a may also be configured to provide corresponding signal containing information about the speed of sound or density measurement related to the process medium 24.

Transducer apparatus or device like element 20 are known in the art; and the scope of the invention is not intended to be limited to any particular type or kind of transducer apparatus or device, and is intended to include other types or kinds of transducer apparatus or devices both now known and later developed in the future.

The scope of the invention is not intended to be limited to any particular type or kind of container or piping or the process medium contained or flowing therein, and is intended to include other types or kinds of containers or pipings or process mediums contained or flowing therein, both now known and later developed in the future.

Calibration

Since the dynamic forces of a vibrating piston, such as piston 20a, can be significant relative to the acoustic reaction force calibration may be required. By way of example, this could be done by simply vibrating the piston 20a in an environment which has low acoustic coupling to measure and then subtract the dynamic piston forces. For example, if the fluid or medium of interest was wet concrete or other water-based slurry, the piston 20a could be operated in air. The acoustic reaction force in air would be very low so the dynamic forces could be measured then subtracted from the total force measured when making the measurement in wet concrete or other water-based slurry.

Calibration techniques are known in the art; and the scope of the invention is not intended to be limited to any particular type or kind of calibration technique, and is intended to include other types or kinds of calibration techniques both now known and later developed in the future.

Model

Figure 1C:
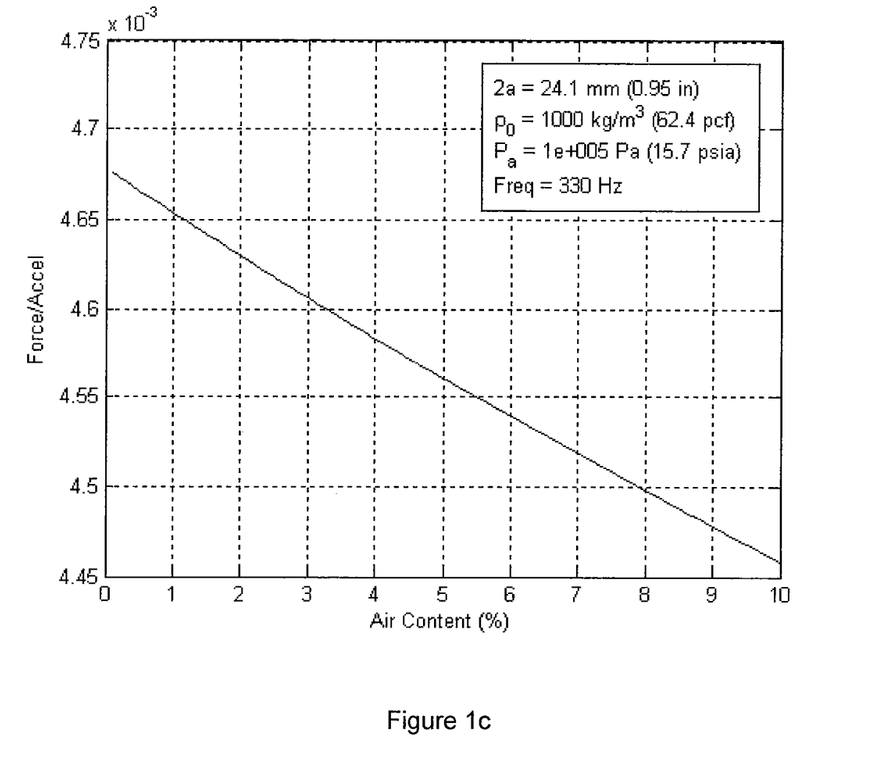
FIG. 1c shows a graph of the force to acceleration versus the volumetric air content (%).

By way of example, equation (4) was modeled, e.g., using MATLAB, and the following curve shows the change in the force to acceleration ratio for a 0.95 inch diameter piston vibrating in aerated water at 330 Hz. Note the relationship between air content and sound velocity was determined using a simplified Wood's equation:

$$c_0 = \sqrt{\frac{P_a}{\phi(1-\phi)\rho_0}} \qquad (8)$$

where:
  $P_a$=absolute pressure, and
  $\phi$=air content or gas void fraction (GVF).

FIG. 1c shows a graph of the force to acceleration versus the volumetric air content (%). Note that at a constant driving force the acceleration increases as the air content is increased. This is due to a reduction in the effective "spring force" of the water due to the compressibility of the air bubbles.

Modeling software or program are known in the art; and the scope of the invention is not intended to be limited to any particular type or kind of modeling software or program, and is intended to include other types or kinds of modeling software or program both now known and later developed in the future.

Test Data

By way of example, in a test procedure, the piston 20a driven by the combination of the voice coil 20d and the linear voice coil actuator 20e was installed in a vertical water column. An accelerometer was attached to the actuator/piston assembly and measured during the test. Also, the current provided by the linear coil actuator 20e to the voice coil 20d which is proportional to the total driving force was measured though an analog output from a voice coil amplifier (not shown). For this simple test, no calibration was completed therefore the force measured includes both the acoustic reaction force and dynamic forces.

Varying amounts of air was bubbled through the vertical water column with the change in height measured to determine the percent air bubbles by volume:

$$\phi = \frac{\Delta h}{\Delta h + H} \qquad (9)$$

Where:
  $\Delta h$=difference between aerated water column height and water only height and
  H=water only height The amount of air bubbles in the water will have a significant effect on the sound velocity of the water with only a minor change in density.

Figure 1D:
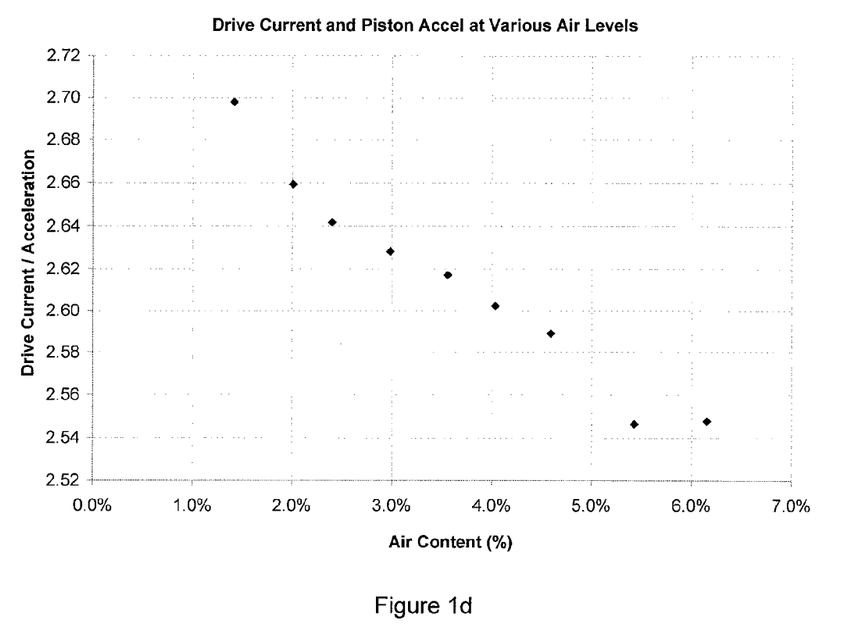
FIG. 1d is a plot is the ratio of the measured current to acceleration versus the volumetric air content.

FIG. 1d is a plot is the ratio of the measured current to acceleration versus the volumetric air content:

Note that this simple test shows the same trend as the aforementioned model, that at a constant driving force as the air content increases the acceleration also increases.

Figure 2A:
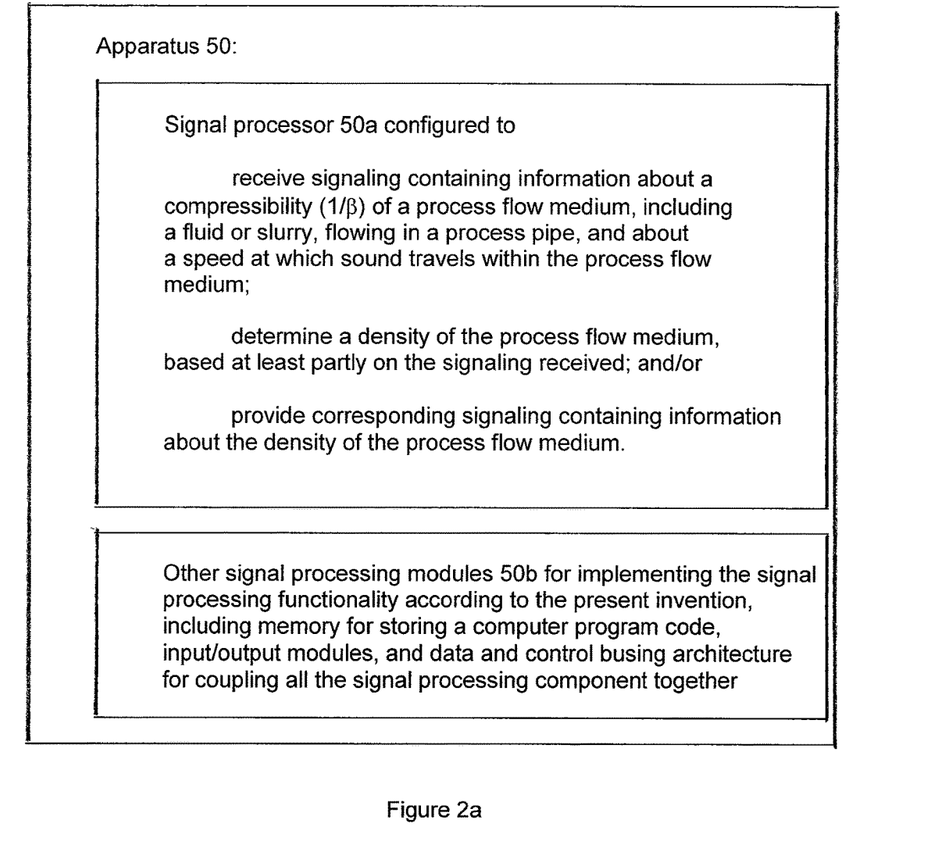
FIG. 2a is a block diagram of a signal processor or signal processing module, according to some embodiments of the present invention.
Figure 2B:
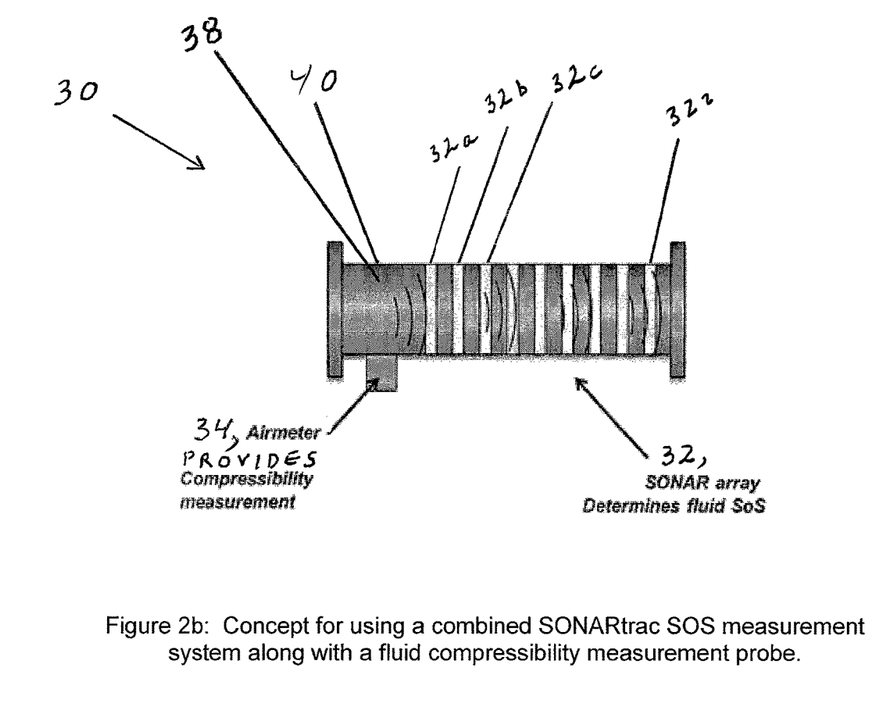
FIG. 2b is a diagram of a process pipe having a device for providing a compressibility measurement and a SONAR-based array for a speed of sound measurement, according to some embodiments of the present invention.

CCS-0095: FIGS. 2a-2b

FIG. 2a shows apparatus generally indicated as 50 according to some embodiments of the present invention. The apparatus 50 may include a signal processor 50a that receives signaling containing information about a compressibility (1/β) of a process flow medium; and determines a density of the process flow medium, based at least partly on the signaling received.

The signal processor or signal processing module 50a may also be configured to providing corresponding signaling containing information about the speed of sound or density measurement related to the process medium.

The objective of this part of the present invention is to provide a determination of the density of the process flow medium or fluid. The speed of sound, c, in a process flow medium or fluid is related to the bulk modulus, β (1/compressibility) and density, ρ, of the process flow medium or fluid via:

$$c = \sqrt{\frac{\beta}{\rho}}$$

Gas entrainment will significantly lower the sound speed in a process flow medium or fluid as the compressibility (1/β) of the fluid increases dramatically with gas void fraction (GVF).

The density of the process flow medium or fluid is thus given by;

$$\rho = \frac{\beta}{c^2}$$

Consequently, a measurement of the speed of sound, combined with a determination of the process flow medium or fluid compressibility can be used to give a measure of the process flow medium or fluid density.

Devices for the measurement of fluid compressibility are known in the art, and the scope of the invention is not intended to be limited to any particular type or kind thereof either now known or later developed in the future. By way of example, FIG. 1b shows a piston arrangement that may be used, or may be adapted to be used without undue experimentation, to provide the measurement of fluid compressibility, consistent with that disclosed herein.

FIG. 2b: An Exemplary Embodiment

By way of example, and according to some embodiments of the present invention, FIG. 2b illustrates and sets forth an approach or apparatus generally indicated as 30, which uses a combined SONARtrac™ or SONAR-based SoS measurement array 32 with a ported unit 34 (aka "airmeter") designed to measure the compressibility (1/β) of a process medium or fluid 36 flowing and/or contained in a container or process flow piping 40. (SONARtrac™ is the name of a SONAR-based product that is known in the art and developed by the assignee of the present application, e.g., that may be configured in relation to a process pipe in order to provide a speed of sound measurement of the medium flowing therein, e.g., consistent with that set forth below in relation to the SONAR-based technology.) SONARtrac™ or SONAR-based SoS measurement array 32 may be configured with bands 32a, 32b, 32c, . . . , 32i, as shown, although the scope of the invention is not intended to be limited to any particular number of bands.

This ported unit 34 may take the form or include a compressibility probe that utilizes a piston like element 20a (see FIG. 1b) that is used to provide a localized compressibility test of the fluid. To make this measurement, the piston may be driven by an actuator like elements 20d and 20e in FIG. 1b) to 'push' it into the process flow medium or fluid. This may be done in an oscillatory fashion, or pulsed at a certain repetition rate. The motion/displacement of the piston is typically understood to be very small in relation to the scale of the pipe 40, etc., comprising typically a displacement of 100-300 microns. As the piston is pushed into the process flow medium or fluid in a repetitive mode, the process flow medium or fluid surrounding the compressibility probe does not have time to respond, and the dynamic response (force to move the piston a given distance) of the piston is determined by the local compressibility of the process flow medium or fluid. To measure this, the force on the piston is measured along with the displacement of the piston (alternatively, the acceleration of the piston can be measured and related back to the piston motion), e.g., consistent with that set forth above in relation to FIGS. 1a to 1d. This gives a measure of the 'spring" constant, or "spring" rate, of the system, which comprises the stiffness of the mechanical assembly supporting the piston and the stiffness of the fluid local to the piston. If the stiffness of the mechanical assembly is known (e.g., through calibration without a backing fluid), the compressibility of the process flow medium or fluid can be inferred from the overall measurement made.

Once the compressibility (1/β) of the process flow medium or fluid and the speed (c) at which sound travels in the process flow medium or fluid are determined, the density (ρ) of the process flow medium or fluid may be provided by the following relationship:

$$\rho = \frac{\beta}{c^2}$$

The SONARtrac™ array 32 may also be used to determine the volumetric flow rate of the medium or fluid flowing in the pipe 40. The combination of a volumetric flow measurement and a density measurement, as provided by this invention, may be further utilized to provide the mass flow of the medium or fluid flowing in the pipe 40.

Ported units like element 34 and or compressibility probes are known in the art. The scope of the invention is not intended to be limited to any particular type or kind of ported units and/or compressibility probes, and is intended to include other types or kinds of ported units and/or compressibility probes both now known and later developed in the future.

The Signal Processor or Signal Processing Module

By way of example, and consistent with that described herein, the functionality of the signal processor or signal processing module 10a, 50a, and/or 20e may be implemented using hardware, software, firmware, or a combination thereof, although the scope of the invention is not intended to be limited to any particular embodiment thereof. In a typical software implementation, the signal processor would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality set forth in the signal processor or signal processing module 10a, such as either determining a speed of sound or density measurement related to the process medium, or a density of the process flow medium, based at least partly on the signaling received, as well as other functionality described herein without undue experimentation. The scope of the invention is not intended to be limited to any particular implementation using technology now known or later developed in the future. Moreover, the scope of the invention is intended to include the signal processor being a stand alone module, as shown, or in the combination with other circuitry for implementing another module.

It is also understood that the apparatus 10 or 50 may include one or more other modules, components, circuits, or circuitry 10b or 50b for implementing other functionality associated with the apparatus that does not form part of the underlying invention, and thus is not described in detail herein. By way of example, the one or more other modules, components, circuits, or circuitry 10b or 50b may include random access memory, read only memory, input/output circuitry and data and address buses for use in relation to implementing the signal processing functionality of the signal processor 10a or 50a, or devices or components related to mixing or pouring concrete in a ready-mix concrete truck or adding chemical additives, etc.

The SONAR-Based Technology

SONAR-based technology is known in the art, including that developed by the assignee of the present application. By way of example, the SONAR-based entrained air meter or arrays may take the form of SONAR-based meter, metering or array technology disclosed, e.g., in whole or in part, in U.S. Pat. Nos. 7,165,464; 7,134,320; 7,363,800; 7,367,240; and 7,343,820, all of which are incorporated by reference in their entirety.

A. Introduction

The known SONAR-based technology includes a gas volume fraction meter (known in the industry as a GVF-100 meter) that directly measures the low-frequency sonic speed (SOS) of the liquid or slurry flowing through a pipe. By way of example, the SONAR-based entrained air meter may take the form of SONAR-based meter and metering technology disclosed, e.g., in whole or in part, in U.S. Pat. Nos. 7,165,464; 7,134,320; 7,363,800; 7,367,240; and 7,343,820, all of which are incorporated by reference in their entirety. Using the Wood's equation, the volume percent of any gas bubbles or the gas void fraction (GVF) is determined from the measured SOS. The Wood's equation requires several other inputs in addition to the measured SOS of liquid/gas mixture. One of the additional inputs in particular, the static pressure of the liquid/gas mixture, can be very important for an accurate calculation of the GVF. To a first order, if the static pressure used for the GVF calculation differs from the actual static pressure of the liquid/gas mixture, then the calculated GVF may typically differ from the actual GVF by 1% as well. For example:

Static Pressure used for GVF calculation=20 psia
Calculated GVF=2%
Actual Static Pressure=22 psia
Static pressure error=22/20−1=0.1=10%
Actual GVF=2%×(1+0.1)=2.2% (10% error)

In many cases, the static pressure of the liquid/gas mixture is available through existing process plant instrumentation. In this case, the measured static pressure can be input directly to the GVF calculation through, e.g., an analog 4-20 mA input in the SONAR-based gas volume fraction transmitter (e.g. GVF-100 meter). Alternatively, a correction to the calculated GVF can be made in the customer DCS for any variation from the fixed pressure that was used to originally calculate the GVF.

In other cases, a static pressure transmitter can be added to the process plant specifically to measure the static pressure used for the GVF calculation. The measured pressure can either be input to the SONAR-based gas volume fraction transmitter (e.g., GVF-1200) or correction made in the DCS as described above.

Occasionally, a the SONAR-based gas volume fraction meter (e.g., GVF-100) may be installed at a location in the process that does not already have a static pressure gauge installed and it is impractical to add one. This could be a location where there is no existing penetration of the pipe to sense the pressure and it would be difficult or expensive to add one. In the case, where a traditional pressure gauge is not available and it is desirable to have a static pressure measurement the following description of a non-intrusive (clamp on) static pressure measurement could be used.

B. Description

For example, according to some embodiments of the present invention, a non-intrusive static pressure measurement may be sensed using traditional strain gauges integrated into the sensor band of the SONAR-based gas volume fraction sensing technology (e.g. the known GVF-100 meter). As the static pressure inside the pipe changes, the static strain on the outside of the pipe also changes. Using a thin-wall assumption for simplicity (t/R<10, where t is the wall thickness and R is the radius) the tangential strain due to internal static pressure is:

$$\varepsilon = \frac{pR}{Et},$$

where ε is the tangential strain (inch/inch), R is the radius (inch), E is the modulus of elasticity (lb/in2) and t is the wall thickness (inch). The radius, wall thickness and modulus is generally known, or at least constant and so if the tangential strain is measured the internal static pressure can be determined.

By way of example, according to one embodiment of the present invention, four strain gauges could be arranged on the sensor band of the SONAR-based gas volume fraction sensing technology (e.g. the known GVF-100 meter) in a Wheatstone bridge configuration to maximize strain sensitivity and minimize temperature effects. In this case, the sensitivity assuming a strain gauge factor of 2, the sensitivity is approximately 13 μV/με, where V is volts. Assuming a 4-inch schedule 40 carbon steel pipe, a one psi change in pressure would cause a 4 μV change in Wheatstone bridge output. This sensitivity would increase for larger diameter pipes which generally have a smaller t/R.

The integrated pressure gauge could be calibrated in-situ for best accuracy, but it may be sufficient to normalize the pressure output to a certain know state then use the tangential strain formula above with know pipe parameters to calculate the pressure from the measured strain.

The SONAR-based entrained air meter, metering or array technology are known in the art and may take the form of a SONAR-based meter disclosed, e.g., in whole or in part in U.S. Pat. Nos. 7,165,464; 7,134,320; 7,363,800; 7,367,240; and 7,343,820, all of which are incorporated by reference in their entirety. The SONAR-based entrained air meter, metering or array technology is capable of providing a variety of information, including the pure phase density and pure phase liquid sound speed is known, such that the GVF can be determined by measuring the speed of sound and then applying the Woods Equation.

Determining the GVF by measuring the speed of sound can provide fast an accurate data. Also the SOS measurement system can be very flexible and can easily be configured to work with different concrete containers and sample particular volumes.

Consistent with that described above, the SONAR-based entrained air meter, metering or array technology are known in the art and may take the form of a SONAR-based meter disclosed, e.g., in whole or in part in U.S. Pat. Nos. 7,165,464; 7,134,320; 7,363,800; 7,367,240; and 7,343,820.

Other Known Technology

The acoustic transmitter, the acoustic receiver or receiver probe and/or transponders are devices that are known in the art, and the scope of the invention is not intended to be limited to any particular type or kind either now known or later developed in the future.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
a transducer apparatus or device that includes:
a piston arranged in a rigid stationary wall, the piston arranged to be in contact with a process medium in a container or piping, and
a motion-sensing transducer having
a linear coil configured to respond to linear coil actuator signaling and vibrate harmonically the piston in contact with the process medium, and
a linear actuator or processor configured to provide the linear coil actuator signaling to vibrate the piston, measure a velocity, acceleration or displacement of the piston, and provide signaling containing information about a sensed radiation impedance of the piston that includes information about the velocity, acceleration or displacement of the piston being measure and a force required to drive the piston being measured; and
a signal processor or signal processing module configured at least to:
receive the signaling containing information about a sensed radiation impedance of the piston; and
determine corresponding signaling containing information about a speed of sound or density measurement related to the process medium, based at least partly on the signaling containing information about a sensed radiation impedance of the piston.

2. Apparatus according to claim 1, wherein the signal processor or signal processing module is configured to determine a speed of sound measurement related to the process medium, based on at least partly on the density of the process medium, the density of the process medium being known, assumed or determined by the signal processor or signal processing module.

3. Apparatus according to claim 1, wherein the signal processor or signal processing module is configured to determine a density measurement related to the process medium, based on at least partly on the speed at which sound travels in the process medium, the speed of sound of the process medium being known, assumed or determined by the signal processor or signal processing module.

4. Apparatus according to claim 3, wherein the signal processor or signal processing module is configured to determine a speed of sound measurement in the process medium based at least partly on a time of flight measurement technique.

5. Apparatus according to claim 3, wherein the signal processor or signal processing module is configured to determine a proper mix or mixture of the process medium based at least partly on a density measurement related to the process medium.

6. Apparatus according to claim 5, wherein the signal processor or signal processing module is configured to determine the proper mix or mixture of a wet concrete, based at least partly determining the density of a wet concrete.

7. Apparatus according to claim 6, wherein the signal processor or signal processing module is configured to determine the density of the wet concrete, based at least partly on knowing, assuming or determining the speed of sound in the wet concrete.

8. Apparatus according to claim 7, wherein the signal processor or signal processing module is configured to determine the speed of sound in the wet concrete based at least partly on a time of flight measurement technique.

9. Apparatus according to claim 1, wherein the signal processor or signal processing module is configured to determine a speed of sound measurement, and is also configured to determine the volume percentage of air contained in the process medium based at least partly on the speed of sound measurement determined.

10. Apparatus according to claim 1, wherein the process medium is a slurry taking the form of a wet concrete, pulp slurry, or food processing slurry.

11. Apparatus according to claim 1, wherein the signal processor or signal processing module is configured to determine the sensed radiation impedance, based at least partly a ratio of the force exerted by a harmonically vibrating piston on the process medium to the velocity of the piston vibrating harmonically.

12. Apparatus according to claim 1, wherein the transducer apparatus or device is configured to act as an acoustic source.

13. Apparatus according to claim 12, wherein the transducer apparatus or device comprises a stationary rigid wall surrounding the piston so as to generate a pressure field in a hemisphere forward of the stationary rigid wall.

14. Apparatus according to claim 12, wherein the transducer apparatus or device comprises either an inline force-sensing transducer configured to measure the force required to drive the piston, or a measuring device configured to measure the electrical power driving the piston.

15. Apparatus according to claim 12, wherein the current going to and driving the linear coil is proportional to the force generated.

16. Apparatus according to claim 1, wherein the signal processor or signal processing module is configured with at least one processor and at least one memory having computer program code, the at least one memory and computer program code configured, with the at least one processor, to cause the apparatus at least to receive the signaling and determine the speed of sound or density measurement related to the process medium, based at least partly on the signaling received.

17. Apparatus according to claim 1, wherein the signal processor or signal processing module is configured to provide the corresponding signal containing information about the speed of sound or density measurement related to the processing medium.

18. Apparatus according to claim 1, wherein
the signaling contains information about a compressibility (1/β) of the process medium and a speed at which sound travels within the process medium; and
the signal processor or signal processing module is configured to determine a density measurement of the process medium, based at least partly on the signaling received.

19. Apparatus according to claim 18, wherein the signal processor or signal processing module is configured to receive first signaling containing information about the compressibility (1/β) of the process medium from the transducer apparatus or device configured to measure the compressibility (1/β) of the process medium.

20. Apparatus according to claim 19, wherein the transducer apparatus or device is configured as a compressibility probe that comprises the piston that is used to provide a localized compressibility test of the process medium.

21. Apparatus according to claim 20, wherein the piston is pushed into the process medium in an oscillatory fashion, or pulsed at a certain repetition rate.

22. Apparatus according to claim 21, wherein the piston has a motion or displacement that is in a range of about 100-300 microns.

23. Apparatus according to claim 20, wherein
the first signaling contains information about a local compressibility of the process flow medium, based at least partly on the fact that, as the piston is pushed into the process medium in a repetitive mode, the process medium surrounding the compressibility probe does not effectively have time to respond; and
the compressibility probe is configured to determine a dynamic response or a force to move the piston a given distance, based at least partly on the first signaling received.

24. Apparatus according to claim 23, wherein the compressibility probe is configured to measure:
the force on the piston, and
either the displacement or acceleration of the piston, where the acceleration of the piston is related back to the motion of the piston.

25. Apparatus according to claim 24, wherein the compressibility probe is configured to determine the local compressibility of the process medium, based at least partly on corresponding measurements providing a measure of a spring constant, or spring rate, of the system, which comprises the stiffness of a mechanical assembly supporting the piston and the stiffness of the process medium local to the piston, so that if the stiffness of the mechanical assembly is known, the local compressibility of the process medium can be inferred from the corresponding measurements made.

26. Apparatus according to claim 18, wherein the signal processor or signal processing module is configured to receive second signaling containing information about the speed at which sound travels within the process medium received from a SONAR-based array that measures the speed at which sound travels within the process medium, based at least partly on the speed at which compressional waves propagate through the process flow medium.

27. Apparatus according to claim 26, wherein the apparatus comprises the SONAR-based array.

28. Apparatus according to claim 27, wherein the SONAR-based array is configured to determine a volumetric flow rate of a process flow medium flowing in a process flow pipe.

29. Apparatus according to claim 28, wherein the signal processor or signal processing module is configured to determine a mass flow of the process flow medium in the process flow pipe, based at least partly on the combination of the volumetric flow measurement and a density measurement.

30. Apparatus according to claim 18, wherein the signal processor or signal processing module is configured to determine the density p of the process medium, based at least partly on the equation:

$$\rho = \frac{\beta}{c^2},$$

where
c is speed of sound speed at which sound travels within the process flow medium and
β is the bulk modulus of the process flow medium.

31. Apparatus according to claim 18, wherein the signal processor or signal processing module is configured with at least one processor and at least one memory having computer program code, the at least one memory and computer program code configured, with the at least one processor, to cause the apparatus at least to receive the signaling and determine the density measurement of the process medium, based at least partly on the signaling received.

32. Apparatus according to claim 18, wherein the signal processor or signal processing module is configured to provide corresponding signal containing information about the density measurement of the process medium.

33. A method comprising:
configuring a transducer apparatus or device having a piston and a motion-sensing transducer that includes a linear coil and a linear actuator by:
arranging the piston in a rigid stationary wall, the piston arranged to be in contact with a process medium in a container or piping, and
responding with the linear coil to linear coil actuator signaling and vibrating harmonically the piston in contact with the process medium,
proving the linear actuator or processor signaling to vibrate the piston,
measuring with the linear actuator or processor a velocity, acceleration or displacement of the piston, and
providing with the linear actuator or processor signaling containing information about a sensed radiation impedance of the piston that includes information about the velocity, acceleration or displacement of the piston being measure and a force required to drive the piston being measured; and configuring a signal processor or signal processing module at least to:

receive the signaling containing information about a sensed radiation impedance of the piston; and determine corresponding signaling containing information about a speed of sound or density measurement related to the process medium, based at least partly on the signaling containing information about a sensed radiation impedance of the piston.

* * * * *